(12) United States Patent
Baldelomar

(10) Patent No.: US 11,241,102 B1
(45) Date of Patent: Feb. 8, 2022

(54) INFANT SECURING SYSTEM

(71) Applicant: Rocio Baldelomar, Cypress, TX (US)

(72) Inventor: Rocio Baldelomar, Cypress, TX (US)

( * ) Notice: Subject to any disclaimer, the term of this patent is extended or adjusted under 35 U.S.C. 154(b) by 0 days.

(21) Appl. No.: 16/714,612

(22) Filed: Dec. 13, 2019

Related U.S. Application Data

(60) Provisional application No. 62/779,153, filed on Dec. 13, 2018.

(51) Int. Cl.
| | | |
|---|---|---|
| A47D 15/00 | (2006.01) | |
| A47D 7/00 | (2006.01) | |
| A47D 9/00 | (2006.01) | |
| A61G 7/05 | (2006.01) | |
| A47D 13/08 | (2006.01) | |
| A61F 5/37 | (2006.01) | |

(52) U.S. Cl.
CPC ............. *A47D 15/008* (2013.01); *A47D 7/00* (2013.01); *A47D 9/00* (2013.01); *A47D 15/005* (2013.01); *A47D 13/08* (2013.01); *A61F 5/3784* (2013.01); *A61G 7/0504* (2013.01); *A61G 7/0526* (2013.01)

(58) Field of Classification Search
CPC ... A47D 7/00; A47D 7/01; A47D 9/00; A47D 13/08; A47D 15/008; A47D 15/01; A47D 15/005; A61F 5/3784; A61G 7/0504; A61G 7/0526
See application file for complete search history.

(56) References Cited

U.S. PATENT DOCUMENTS

| | | | | |
|---|---|---|---|---|
| 857,507 | A * | 6/1907 | Wilson | A41B 13/06 128/873 |
| 1,502,276 | A * | 7/1924 | Siebert | A47D 15/008 128/875 |
| 1,802,540 | A * | 4/1931 | Schmidt | A47D 15/008 2/114 |
| 1,964,271 | A * | 6/1934 | O'Dwyer | A47G 9/083 128/873 |
| 2,850,746 | A * | 9/1958 | Foehner | A47D 15/008 5/494 |
| 3,845,513 | A * | 11/1974 | Hubner | A47G 9/083 2/69.5 |
| 3,872,524 | A * | 3/1975 | Hummel | A47D 15/008 2/69.5 |
| 4,202,052 | A * | 5/1980 | Bilanzich | A47D 15/008 2/114 |
| 4,853,996 | A * | 8/1989 | Harrigan | A61F 5/3776 5/494 |
| 4,911,105 | A * | 3/1990 | Hocum | A47D 15/008 128/875 |
| 7,150,054 | B1 * | 12/2006 | Byrne | A47D 15/008 5/494 |
| 8,032,961 | B1 * | 10/2011 | Downs | A47D 15/008 5/655 |
| 8,117,698 | B1 * | 2/2012 | Khaze Harry | A47D 15/008 5/655 |

(Continued)

*Primary Examiner* — Peter M. Cuomo
*Assistant Examiner* — Rahib T Zaman
(74) *Attorney, Agent, or Firm* — Leavitt Eldredge Law Firm

(57) ABSTRACT

An infant securing system includes a bed sheet with a top surface; at least two straps secured to a back of the bed sheet to secure underneath a mattress to secure the bed sheet in place; a vest sewn to the top surface, the vest having a closure to secure around an infant to keep the infant in an upright position; the infant is secured via the vest.

2 Claims, 6 Drawing Sheets

(56) References Cited

U.S. PATENT DOCUMENTS

| | | | | |
|---|---|---|---|---|
| 8,276,224 | B1* | 10/2012 | von Yurt | A47G 9/0246 5/494 |
| 8,302,230 | B1* | 11/2012 | Jarrett, Jr | A47D 15/02 5/655 |
| 8,572,782 | B1* | 11/2013 | Amini | A47G 9/04 5/655 |
| 2004/0199999 | A1* | 10/2004 | Landry | A47D 15/02 5/494 |
| 2005/0236002 | A1* | 10/2005 | Cooley | A47D 5/00 128/845 |
| 2007/0061968 | A1* | 3/2007 | Fader | A47D 15/008 5/494 |
| 2007/0266498 | A1* | 11/2007 | Lord | A47D 15/008 5/655 |
| 2009/0313757 | A1* | 12/2009 | Walsh-Barltrop | A61F 5/3784 5/424 |
| 2010/0275373 | A1* | 11/2010 | Kaplan | A41B 13/06 5/494 |
| 2012/0060285 | A1* | 3/2012 | Herman | A47C 21/022 5/498 |
| 2012/0159707 | A1* | 6/2012 | Ortega | A47D 15/008 5/95 |
| 2012/0192353 | A1* | 8/2012 | Marlowe | A47D 15/005 5/655 |

\* cited by examiner

INFANT SECURING SYSTEM

BACKGROUND

Field of the Invention

The present invention relates generally to infant bed systems, and more specifically, to a removable harness system for ensuring infants stay on their backs while asleep.

Description of Related Art

Infant bed systems are well known in the art and provide means for infants to sleep comfortably. For example, FIG. 1 depicts a conventional infant bed system 101 having a crib 103 with a mattress 105 on which an infant 107 sleeps. It should be appreciated that the styles of infant cribs and beds can vary, however, one known problem is that infants must sleep on their back in order to be safe from suffocation. In conventional systems, the infant may roll over to their stomach, thereby causing the possibility of suffocation and harm to the infant.

Accordingly, although great strides have been made in the area of infant bed systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
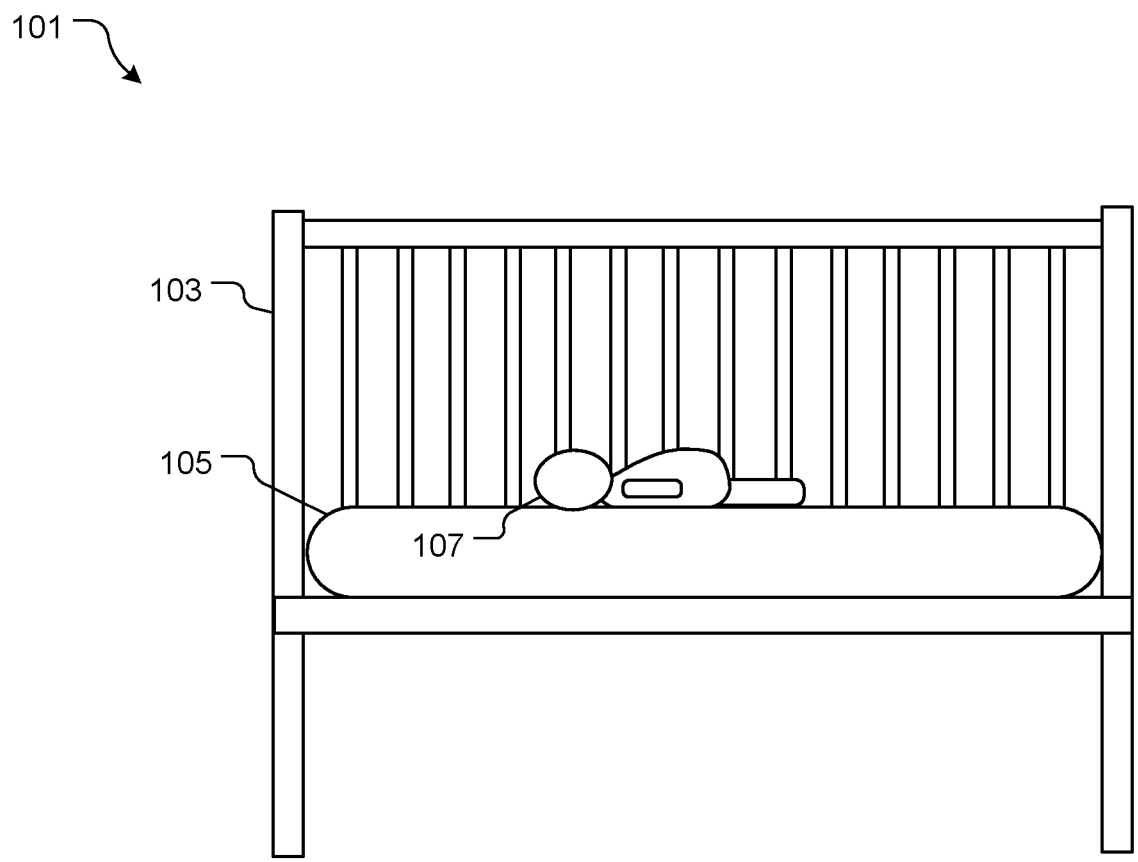
FIG. 1 is a side view of a conventional infant bed system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional infant bed systems. Specifically, the system keeps the infant asleep on their back. In addition, the system secures across the back of the bed's mattress in order to keep the system in place. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
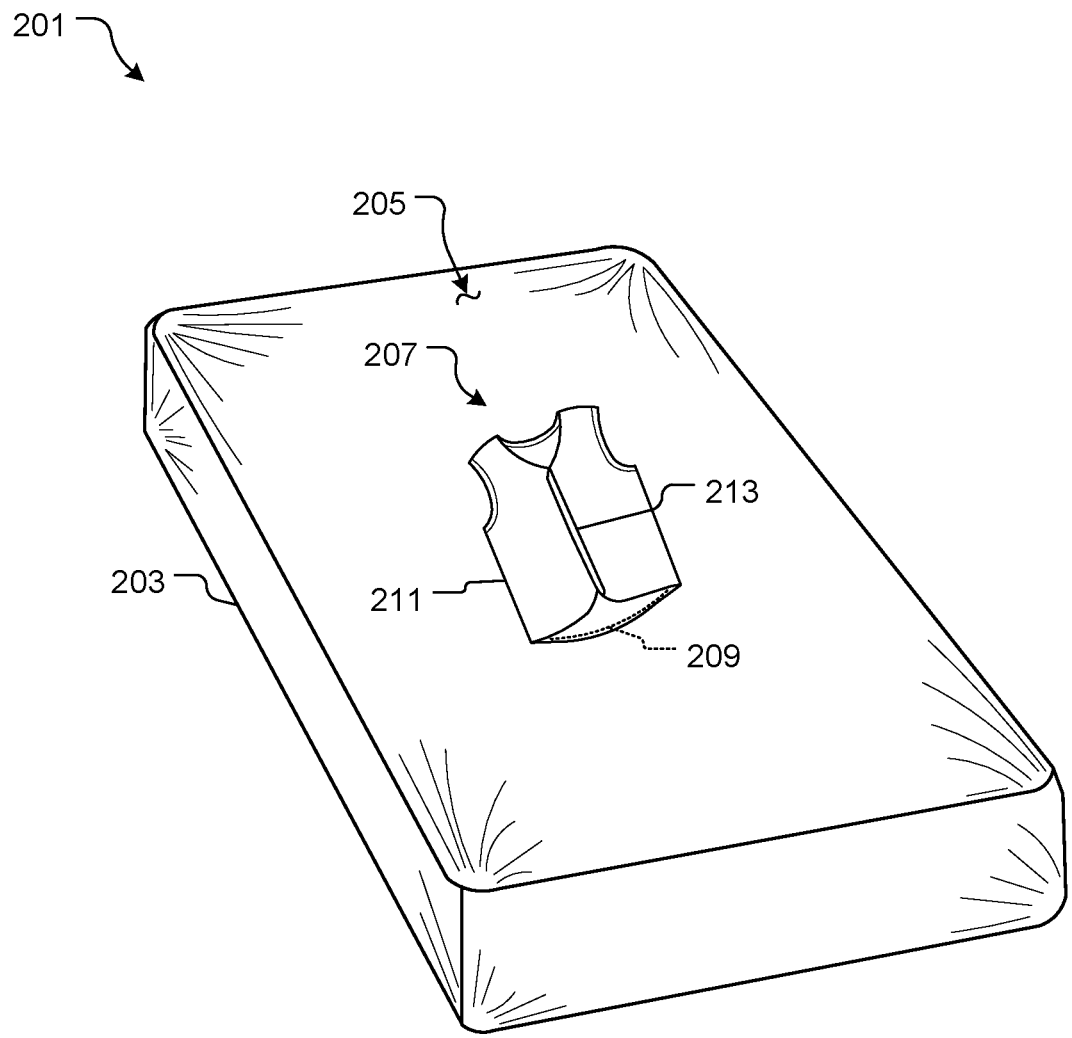
FIG. 2 is an isometric view of an infant securing system in accordance with a preferred embodiment of the present application.
Figure 3:
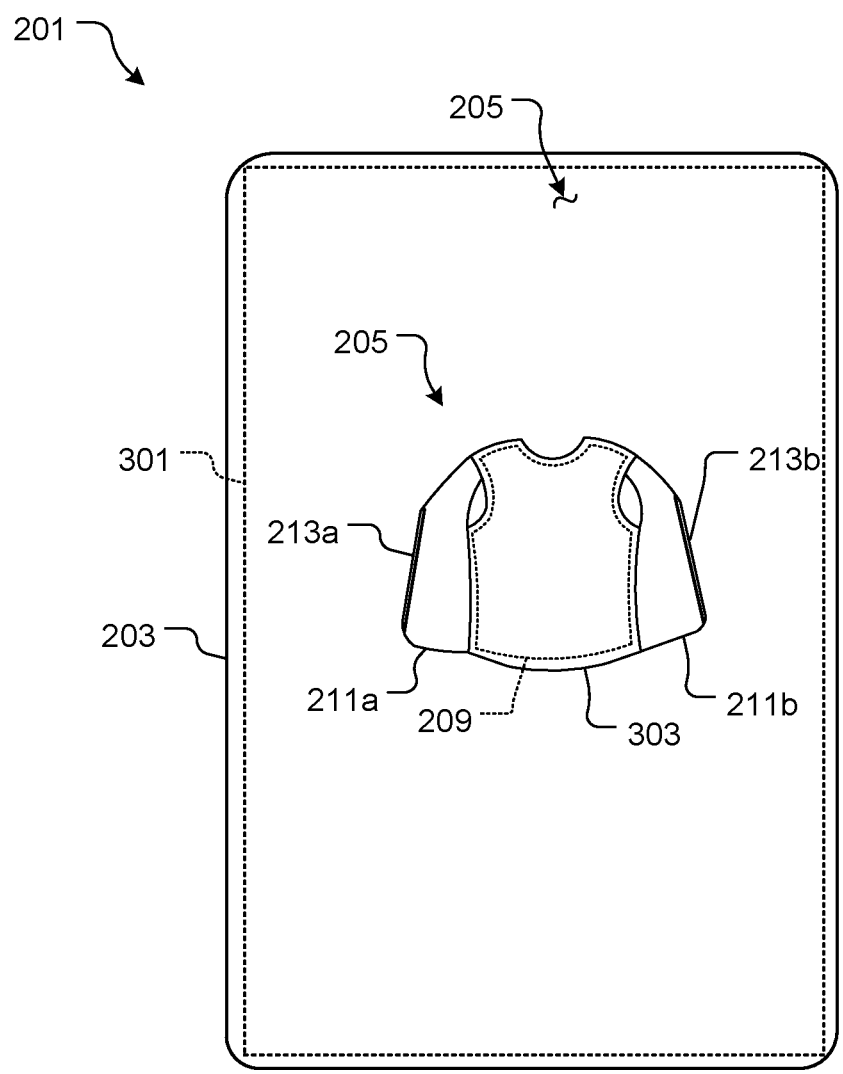
FIG. 3 is a top view of the system of FIG. 2.
Figure 4:
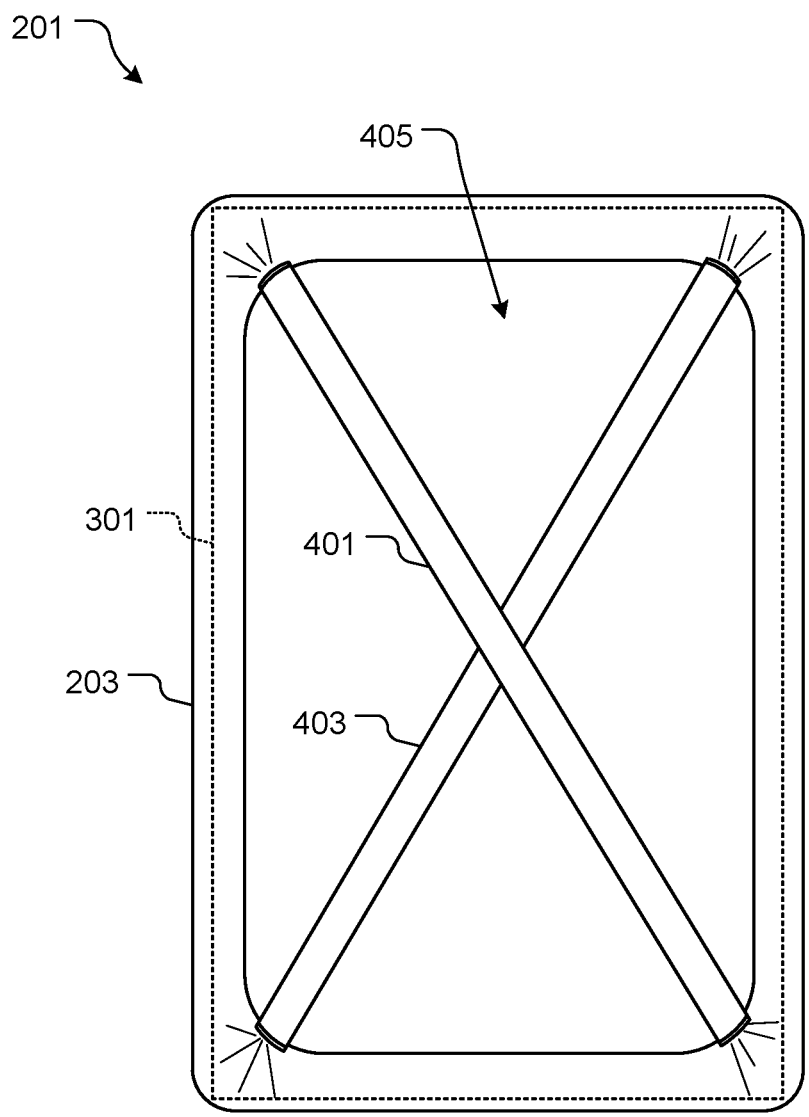
FIG. 4 is a bottom view of the system of FIG. 2.

Referring now to the drawings wherein like reference characters identity corresponding or similar elements throughout the several views, FIGS. 2-4 depict various views of an infant securing system 201 in accordance with a preferred embodiment of the present application. It will be appreciated that system 201 overcomes one or more of the above-listed problems commonly associated with conventional infant bed systems.

In the contemplated embodiment, system 201 includes a sheet 203 having a top surface 205 on which a vest 207 is secured. The vest 207 includes an attachment device 209 to secure to the sheet. In some embodiments, the vest 207 is permanently secured via a means such as sewing/stitching, however, in other embodiments, the vest 207 is removable, such as through hook and loop fasteners or the like. The vest 207 includes a main body portion 211 that includes a closure 213 to secure around the body of the infant. The closure 213 can be a zipper, buttons, hook and loop fasteners, or the like. It should further be appreciated that the vest can vary in shape and size as is desirable for ensuring a comfortable fit on the infant. In the preferred embodiment, the vest 207 is composed of a soft, and breathable material, thereby further ensuring that comfort.

One of the unique features believed characteristic of the present application is the use of a vest secured to a sheet, which provides for easy securing of the infant to the bed sheet, and further ensures infant comfort and safety.

In FIG. 3, a simplified top view depicts system 201 with vest 207 in an open configuration. Vest 207 includes body 211 with closure 213 and a back portion 303 secured to sheet 203 secured directly to mattress 301.

In FIG. 4, a back view of system 201 is shown. As shown, in the preferred embodiment, system 201 includes two straps 401, 403 composed of an elastic material and attached to sheet 203, wherein the straps 401, 403 are configured to crisscross on a back side 405 of the mattress. This feature ensures that the sheet remains secured to the mattress 301 and thereby again provides for improved safety of the system.

Figure 5:
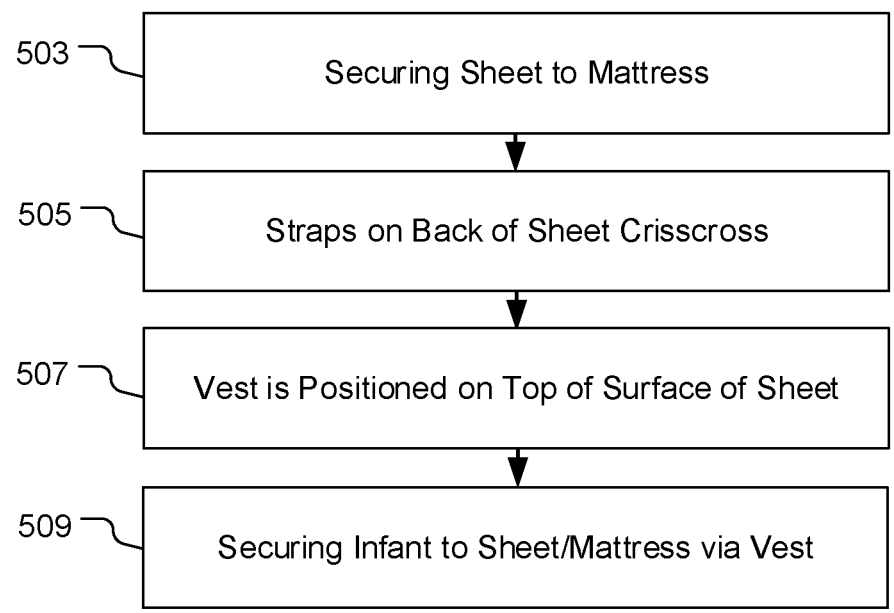
FIG. 5 is a flowchart of the method of use of the system of FIG. 2.

In FIG. 5, a flowchart 501 depicts a method of use of system 201. During use, the sheet is secured to the mattress such that the straps crisscross in the back and the vest is presented on a top surface of the sheet, as shown with boxes 503, 505, 507. The infant is then secured to the sheet via the vest, as shown with box 509.

Figure 6:
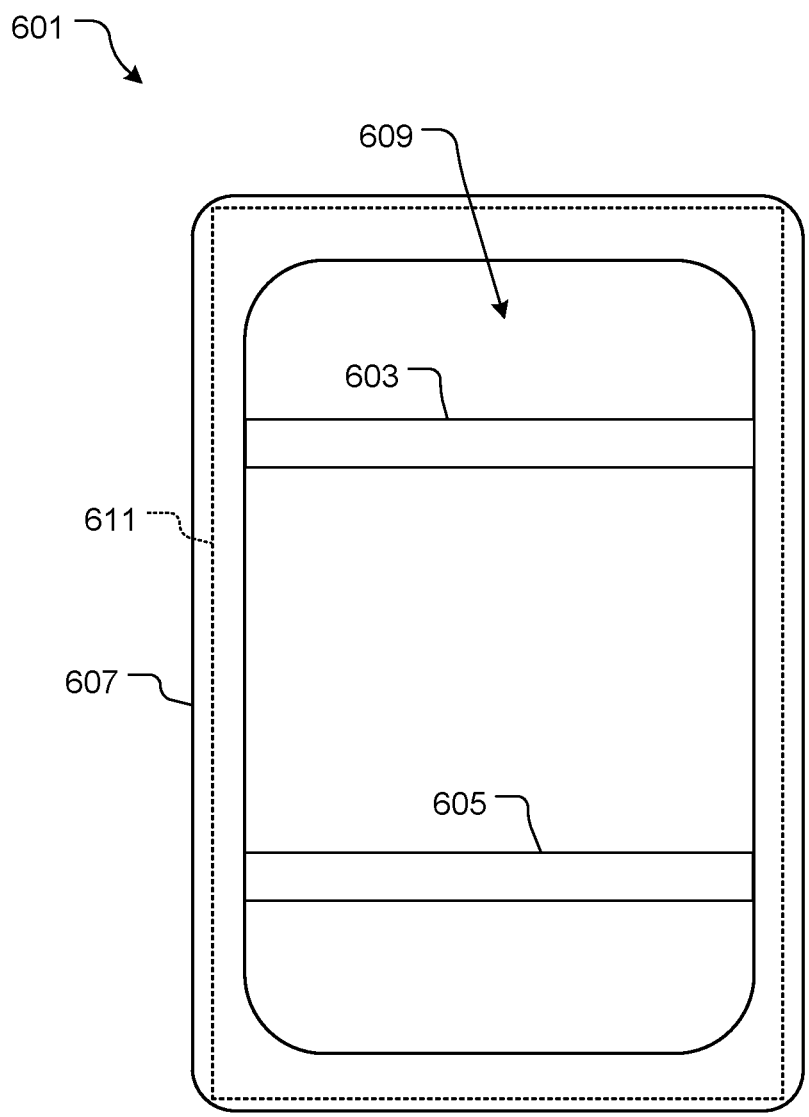
FIG. 6 is a bottom view of an alternative embodiment of the infant securing system in accordance with the present application.

In FIG. 6, a back view of an alternative embodiment of a system 601 is shown. It should be appreciated that system 601 includes all of the features discussed above, but merely includes an alternate configuration of straps 603, 605. As shown, two straps 603, 605 composed of an elastic material and attached to sheet 607, wherein the straps 603, 605 are configured run horizontal on the back side 609 of the mattress 611. This feature ensures that the sheet remains secured to the mattress 611 and thereby again provides for improved safety of the system.

It should be appreciated that one of the unique features believed characteristic of the present application is that the infant can be securely placed in a bed without the risk of the infant rolling over and being susceptible to Sudden Infant Death Syndrome.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An infant securing system, consisting of:
   a bed sheet with a top surface, the bed sheet is configured to completely enclose a top surface and sides of a mattress, the bed sheet having four corners;
   at least two straps secured to a back of the bed sheet and configured to secure the bed sheet in place, the at least two straps are positioned at a bottom surface of the mattress, the at least two straps overlap each other to form a cross-shaped configuration, the at least two straps secure to the four corners of the bed sheet, which in turn prevents the bed sheet from moving relative to the mattress;
   a vest removably secured to the top surface via a fastener, the vest consisting of:
      a back portion to secure flat against the top surface of the bed sheet;
      a main body portion having a first side and a second side, the first side and the second side extending from the back portion; and
      a closure to close the first side and the second side together around an infant to keep the infant in an upright position;
      wherein the main body portion is open at a bottom and secures only around a torso of the infant;
   wherein the infant is secured to the mattress via the vest and the bed sheet; and
   wherein the vest removes from the bed sheet via the fastener.

2. A method of securing an infant to a bed, the method comprising:
   providing the system of claim 1;
   securing the infant securing system to the mattress; and
   placing the vest on an infant to secure the infant to the bed sheet and mattress;
   wherein the infant is secured to the mattress via the vest to prevent the infant from rolling onto their stomach.

\* \* \* \* \*